(12) United States Patent
Atallah et al.

(10) Patent No.: US 10,342,910 B2
(45) Date of Patent: Jul. 9, 2019

(54) DEVICE AND METHOD FOR PREDICTING INTRADIALYTIC PARAMETERS

(71) Applicant: B. BRAUN AVITUM AG, Melsungen (DE)

(72) Inventors: Richard Atallah, Melsungen (DE); Janosch Henze, Kassel (DE); Christof Strohhoefer, Kassel (DE)

(73) Assignee: B. Braun Avitum AG (DE)

( * ) Notice: Subject to any disclaimer, the term of this patent is extended or adjusted under 35 U.S.C. 154(b) by 457 days.

(21) Appl. No.: 14/454,084

(22) Filed: Aug. 7, 2014

(65) Prior Publication Data

US 2015/0045713 A1 Feb. 12, 2015

(30) Foreign Application Priority Data

Aug. 7, 2013 (DE) .......................... 10 2013 108 543

(51) Int. Cl.
| | |
|---|---|
| A61M 1/16 | (2006.01) |
| A61M 1/36 | (2006.01) |
| A61B 5/021 | (2006.01) |
| A61B 5/00 | (2006.01) |
| G06N 3/08 | (2006.01) |
| A61M 1/14 | (2006.01) |
| G16H 50/50 | (2018.01) |

(52) U.S. Cl.
CPC ........... *A61M 1/1603* (2014.02); *A61B 5/021* (2013.01); *A61B 5/4839* (2013.01); *A61M 1/14* (2013.01); *A61M 1/1613* (2014.02); *A61M 1/3609* (2014.02); *G06N 3/08* (2013.01); *G16H 50/50* (2018.01); *A61M 2205/3334* (2013.01); *A61M 2205/3368* (2013.01); *A61M 2230/005* (2013.01); *A61M 2230/207* (2013.01); *A61M 2230/208* (2013.01); *A61M 2230/30* (2013.01)

(58) Field of Classification Search
None
See application file for complete search history.

(56) References Cited

U.S. PATENT DOCUMENTS

| | | | |
|---|---|---|---|
| 6,423,022 | B1 | 7/2002 | Roeher et al. |
| 6,579,241 | B2 | 6/2003 | Roeher |
| 7,033,539 | B2 | 4/2006 | Krensky et al. |

(Continued)

FOREIGN PATENT DOCUMENTS

| | | |
|---|---|---|
| CN | 101516417 A | 8/2009 |
| CN | 102159260 A | 8/2011 |

(Continued)

OTHER PUBLICATIONS

Krepel et al. "Variability of relative blood volume during haemodialysis", Nephrol Dial Transplant (2000) 15: 673-679.*

(Continued)

*Primary Examiner* — Li Wu Chang
(74) *Attorney, Agent, or Firm* — RatnerPrestia

(57) ABSTRACT

Devices and methods for the prognosis of intradialytic parameters such as a blood pressure are described, wherein at least one learning algorithm and/or at least one neural network is/are provided. A memory device stores patient-individual intradialytic parameters, laboratory parameters, and/or machine parameters, which can be used in the prognosis of patient-specific parameter progress during a dialysis treatment.

15 Claims, 6 Drawing Sheets

(56) References Cited

U.S. PATENT DOCUMENTS

| | | | |
|---|---|---|---|
| 7,785,463 B2 * | 8/2010 | Bissler | A61M 1/16 210/143 |
| 8,551,342 B2 | 10/2013 | Moissl et al. | |
| 8,556,819 B2 | 10/2013 | Roeher et al. | |
| 2002/0068015 A1 | 6/2002 | Polaschegg et al. | |
| 2007/0038191 A1 | 3/2007 | Burbank et al. | |
| 2007/0175827 A1 | 8/2007 | Wariar | |
| 2008/0067132 A1 * | 3/2008 | Ross | A61B 5/02007 210/739 |
| 2009/0055333 A1 * | 2/2009 | Wang | G06F 19/345 706/17 |
| 2010/0016776 A1 | 1/2010 | Roher et al. | |
| 2011/0163034 A1 * | 7/2011 | Castellarnau | A61M 1/16 210/646 |
| 2012/0273354 A1 | 11/2012 | Orhan et al. | |
| 2012/0277551 A1 | 11/2012 | Gerber et al. | |
| 2013/0081998 A1 * | 4/2013 | Chamney | A61M 1/16 210/647 |
| 2013/0331712 A1 * | 12/2013 | Moissl | A61M 1/16 600/483 |

FOREIGN PATENT DOCUMENTS

| | | |
|---|---|---|
| DE | 198 21 534 | 8/1999 |
| DE | 100 47 421 | 1/2003 |
| DE | 10 2008 010 531 | 8/2009 |
| DE | 10 2009 018 649 | 10/2010 |
| EP | 0 956 872 | 11/1999 |
| EP | 1 226 838 | 7/2002 |
| EP | 1 514 562 | 3/2005 |
| EP | 1 844 800 | 10/2007 |
| EP | 2 061 532 | 5/2009 |
| WO | WO 2010/028860 | 3/2010 |
| WO | WO 2011/080185 | 7/2011 |
| WO | WO 2011/080190 | 7/2011 |

OTHER PUBLICATIONS

Franssen et al. "Automatic feedback control of relative blood volume changes during hemodialysis improves blood pressure stability during and after dialysis", Hemodialysis International 2005; 9: 383-392.*

German Search Report for DE 10 2013 108 543.1 dated Feb. 11, 2014.

MEdizinische DAtenanalyse mit neuronalen Netzen, URL: http://medan.de

European Search Report for EP 14179679.7 dated Dec. 12, 2014.

Fernandez et al., "Dialysate-side urea kinetics. Neural network predicts dialysis dose during dialysis," Medical & Biological Engineering & Computing, Jul. 2003, vol. 41, pp. 392-396. XP019834524.

Hongwei Liu, "On the Levenberg-Marquardt training method for feed-forward neural networks," Natural Computation (ICNC), 2010 Sixth Intl. Conf. on, IEEE, Aug. 2010, pp. 456-460. XP0031761478.

Safavieh et al., "Forecasting the Unknown Dynamics in NN3 Database Using a Nonlinear Autoregressive Recurrent Neural Network," Neural Networks, 2007, Intl. Joint Conf on, IEEE, Aug. 2007, pp. 2105-2109. XP031154919.

Mirikitani et al., "Recursive Bayesian Levenberg-Marquardt Training of Recurrent Neural Networks," Neural Networks, 2007, Intl. Joint Conf. on, IEEE, Aug. 2007,.pp. 282-287. XP031154605.

DE Office Action with English translation for Application No. 14 179 679.7, dated Nov. 22, 2016, 13 pages.

Chinese First Office Action for Chinese Application No. 201410366994.9, dated Aug. 31, 2017, including English translation, 19 pages.

Chinese Office Action for Chinese Application No. 201410366994.9, dated May 4, 2018, including English translation, 20 pages.

* cited by examiner

Prognosis of the blood pressure by means of different network types

Prognosis of the blood pressure by a network with different training algorithms

Fig. 11   Prognosis of the blood pressure with and withoutime lag
for different learning algorithms
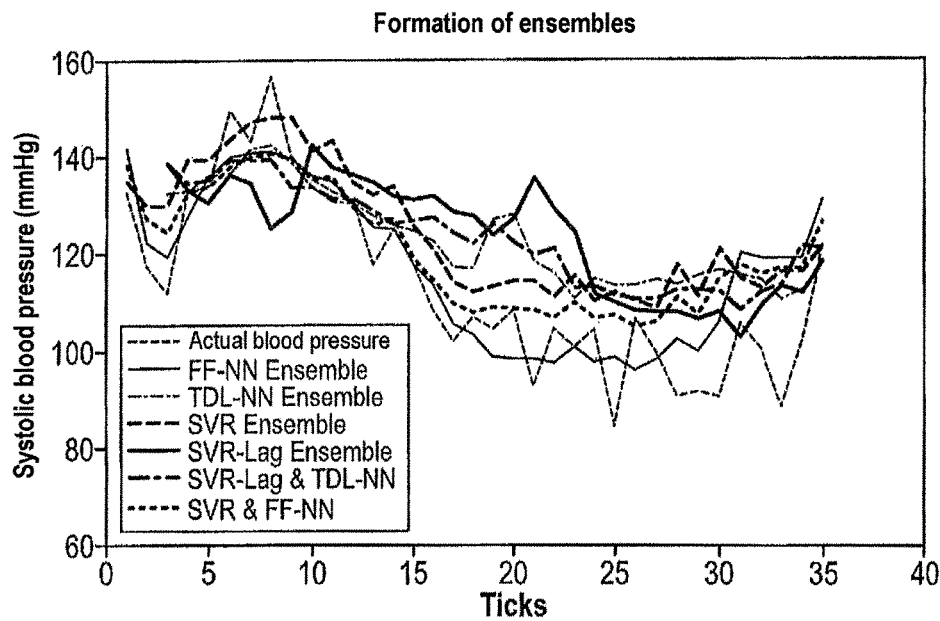
Fig. 12
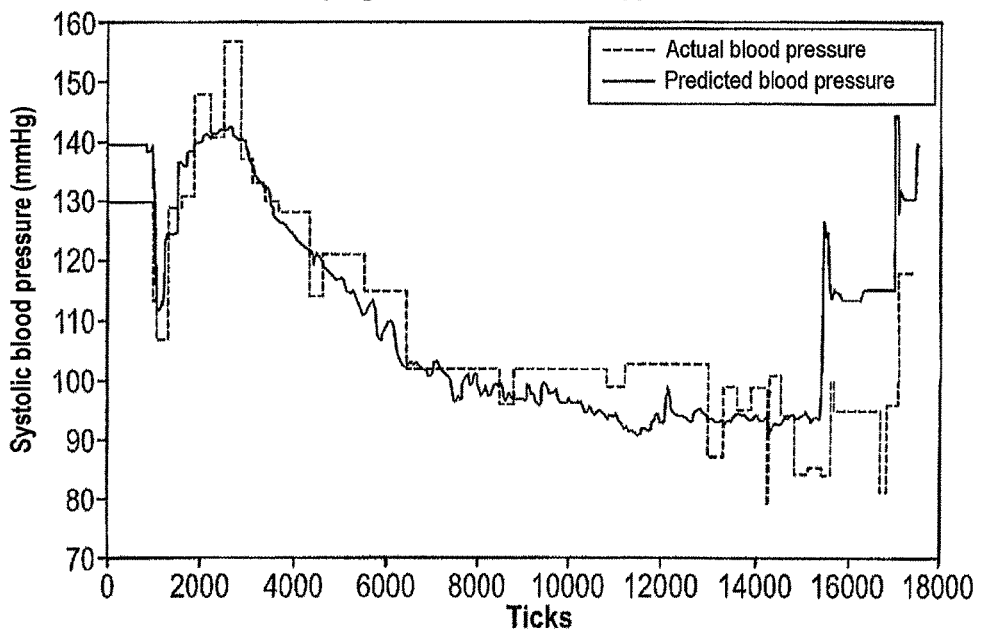

DEVICE AND METHOD FOR PREDICTING INTRADIALYTIC PARAMETERS

CROSS REFERENCE TO RELATED APPLICATIONS

This application claims priority to German application DE 10 2013 108 543.1 filed Aug. 7, 2013, the contents of such application being incorporated by reference herein.

FIELD OF THE INVENTION

The invention relates to a device and a method for predicting intradialytic parameters such as blood pressure.

BACKGROUND

Hitherto, problems in medical treatment, such as intradialytic hypotensive situations for example, have been reduced or corrected by retrospective control. Thus, an intervention such as the reduction of the ultrafiltration rate (UF rate) has only been performed in the event of a hypotensive episode.

Symptomatic, intradialytic hypotensive situations pertain to the most common complications during dialysis treatment. One of the main causes of these hypotensive situations is the imbalance between the UF rate and the refill process, i.e. the subsequent flow of water from the intracellular space and the interstitium into the intravasal space. For the purpose of reducing and avoiding such hypotensive situations, various techniques have been developed, which are based on biofeedback systems. Possible control parameters for stabilizing the hemodynamic circulation of the patient are e.g. the blood pressure (BD) and the relative blood volume (RBV). Candidates for adjustable parameters are the temperature (DT) of the dialysis liquid, the ultrafiltration rate (UFR or UF rate), and the conductivity (LF) of the dialysis liquid. All these control parameters or adjustment parameters coalesce in different combinations and with various reciprocal effects.

DESCRIPTION OF THE RELATED ART

A biofeedback system described in EP 0 956 872 A2, EP 1 226 838 A2 and EP 1 844 800 B1 controls the direct cause of hypotensive situations, i.e. the blood pressure.

WO 2011/080185 and WO 2011/080190 describe measuring equipment for predicting a drop in blood pressure. Here, the heart rate amplitude is calculated with various signals recorded by the machine and/or directly on the patient, which amplitude results in a variance. The variance provides insights into the occurrence of a hypotensive event.

EP 2 061 532 B1 describes therapy equipment with a memory-supported control device, the progress of the blood pressure from preceding therapy units is examined in terms of any similarity to the current blood pressure progress at the current point in time. From among those curves which have the greatest similarity, at least one curve is selected, which shows a blood pressure drop, and said curve will be the pilot variable of anticipatory blood pressure control. In doing so, however, there is a chance that a curve is selected in the test, which has very little similarity and yet will be applied as the pilot curve for the current therapy unit.

However, the above-mentioned biofeedback systems only show retrospective reaction, i.e. react only after the occurrence of a hypotensive episode. A drop in blood pressure cannot be predicted hereby.

When blood volume is controlled, it is continuously measured and, with the control of the UF and LF, made to follow a predefined blood volume progress by force; the blood volume may fluctuate around said predefined progress only in a predefined interval. This is achieved with adaptive MIMO (Multi Input Multi Output) control.

In another biofeedback system, the arterial and venous temperatures are recorded by temperature sensors installed in the machine. By changing the temperature of the dialysis liquid, the difference between the recorded arterial and venous temperatures is controlled so that it adopts the target value. As a consequence of this, there is a change in venous or extracorporeal temperature. Indeed, this allows the achievement of a stable condition in the patient, but the controlling of the temperature does not deliver any direct information on the current condition of the patient.

EP 0 956 872 A2 (EP 0956 872 B1) describes the control of blood pressure, based on monitoring the blood pressure of the patient in defined time intervals. According to the blood pressure progress and the current blood pressure, and depending on two predefined limits, the UF rate is adjusted. This biofeedback system also involves a retrospective reaction. The UF rate is not adjusted until drops in blood pressure have been detected.

EP 1 844 800 B1 describes the time-flexible control of blood pressure, which receives substituted blood pressure values from previous, patient-specific blood pressure progress at defined points in time. This allows a reduction in the number of blood pressure measurements within a therapy unit.

EP 0956 872 A2 (EP 0956 872 B1), EP 1 844 800 B1 and EP 2 061 532 B1 each require a certain number of current blood pressure measurements so as to allow the start of a comparison with preceding therapy units. This results in the disadvantage that a blood pressure drop may have occurred by then.

WO 2011/080185 and WO 2011/080190 describe the prognosis of a blood pressure drop which is indicated by a warning signal. This signal informs the staff to take countermeasures. If the prognosis of hypotension is incorrect, the staff are informed unnecessarily, resulting in a waste of time and putting the patient under stress in the event of countermeasures such as the Trendelenburg position.

SUMMARY OF THE INVENTION

The invention relates to an object to provide a device and a method, which are able to increase the treatment quality during treatment.

Exemplary embodiments of the invention relate to the prognosis of intradialytic parameters such as the blood pressure (BD). The prognosis may take place with the aid of learning algorithms, for instance with neural networks. This prognosis allows the staff to have a view of the future performance of the patient parameters, so that measures can be taken early, or timely automatic intervention by the machine can occur.

According to one aspect of the invention, a device is made available for the prognosis of intradialytic parameters such as the blood pressure, at least one learning algorithm and/or at least one neural network being provided. A memory device is capable of storing patient-individual intradialytic parameters, laboratory parameters, and/or machine parameters, which can be used in the prognosis of patient-specific parameter progress during dialysis treatment.

The patient-individual intradialytic parameters may be, for example, the blood pressure and/or the relative blood volume (RBV). The laboratory parameters are albumin and/or urea, for instance. The machine parameters are the venous pressure (PV) and/or the arterial pressure (PA), for example.

It is advantageous to display a trend in the progress of the desired parameter, e.g. visually or acoustically, so that the treatment staff can be immediately informed.

A biofeedback system which uses the prognosis as an input allows countermeasures to be taken automatically and as quickly as possible, e.g. in the form of a UF reduction, an LF change, a modification of the temperature of the dialysis liquid or an injection of an isotonic solution.

Preferably, it is possible to provide at least one sensor or memory arrangement for detecting or storing machine parameters such as venous pressure (PV), arterial pressure (PA), transmembrane pressure (TMP), conductivity (LF) of the dialysis liquid, temperature (DT) of the dialysis liquid, and/or further parameters, and/or a sensor arrangement or memory arrangement for detecting patient parameters such as the absorbance of uremic toxins, of the hematocrit (HCT), and/or a sensor arrangement or memory arrangement for detecting or storing laboratory parameters such as albumin, urea etc.

The provided training unit and prognosis unit allow the determination of the prognosis accuracy, the training unit being preferably designed to carry out a learning phase first, whereupon it forwards the correspondingly trained, i.e. correspondingly adapted, values of a training algorithm to the prognosis unit. Then, the integrated training algorithm allows the prognosis unit to perform a prediction based on extrapolations or other calculations for the prognosis of the future progress of parameters to be determined or monitored. The prognosis parameters may be evaluated, compared with threshold values, and/or displayed, so that optimized, quick evaluation and information are achievable.

Preferably, the training unit, the prognosis unit and/or a means for forming prognosis parameters may each be designed as an artificial neural network. As an alternative or in addition, it is possible to use support vector machines.

As an option, an alarm unit for outputting a warning, e.g. in acoustic and/or visual form and/or in the form of a display may be provided on which the current progress of the prognosis parameters can be represented, as well as the estimated progress to be expected in future.

In one or more exemplary embodiments, a controller is provided, which is able to take control interventions based on the prognosis parameters as well as on the current parameters, for example the blood pressure or the relative blood volume, so that a quick, precise corrective intervention can be carried out in case of need.

During the initial phase, the structure of a neural network comprising an input layer with at least two inputs, at least one hidden layer comprising at least three neurons, and at least one output layer with at least one output can be adapted and trained, and the outputs can be adapted to input data.

In this process, weights of the predefined network can be calculated and updated.

It is also possible to automatically alter the structure of the network, e.g. the number of the neurons or hidden layers, in order to ensure an optimized learning process with an existing data record, and to adapt the learning algorithm.

The networks may be trained with the Bayesian Regulation Backpropagation and Levenberg-Marquardt Backpropagation algorithms as the training algorithms. The NAR or NARX network may be used for the training algorithm.

A further improvement in the prognosis can be achieved by involving at least one or more of the following input parameters in addition to blood pressure, namely the ultrafiltration rate, UF rate; ultrafiltration volume; arterial and venous pressure; hematocrit; relative blood volume; oxygen saturation; hemoglobin; ultrafiltration rate; heartbeat; absorbance of uremic toxins; systolic blood pressure; conductivity of the dialysis liquid (acid and base conductivity, pH value), and/or temperature of the dialysis liquid, and/or further learning techniques.

A further aspect of the invention relates to a method for predicting intradialytic parameters such as a blood pressure, at least one learning algorithm and/or at least one neural network being provided, patient-individual intradialytic parameters, laboratory parameters and/or machine parameters being stored and used in the prognosis of patient-specific parameter progress during a dialysis treatment. The patient-individual intradialytic parameters may be the blood pressure and/or the relative blood volume (RBV). The laboratory parameters are e.g. albumin and/or urea, and/or the machine parameters are e.g. the venous pressure (PV) and/or the arterial pressure (PA). It is possible to display a trend in the progress of the desired parameter or the progress itself, for instance visually or acoustically.

By storing patient-individual intradialytic parameters (e.g. BD, RBV, . . . ), laboratory parameters (e.g. albumin, urea, . . . ) and machine parameters (e.g. venous pressure (PV), arterial pressure (PA), . . . ), it is possible to predict patient-specific parameter progress during a dialysis treatment. A parameter which is relevant here may be the blood pressure. This prognosis gives the user future information about the condition of the patient, so that the user (e.g. the staff) may interact early, by adjusting one or more dialysis or patient parameters. If the blood pressure progress of the patient is predicted, the user or operator, e.g. a user or therapist such as a physician or a hospital nurse, receives information on how the blood pressure will behave within the near future, e.g. within the next minutes or hours, with the given parameters, e.g. the UF rate. If the predicted blood pressure progress is critical in terms of a possible hypotensive episode, there is the possibility in advance to eliminate it by arranging the automatic or manual reduction of the UF rate, for example.

In one, more or all exemplary embodiments, the prognosis of the intradialytic blood pressure (BD) is possible on the basis of patient-individual, stored physiological parameters, which enables the early control of the blood pressure and hence allows the prevention of a falling blood pressure trend and a reduction in hypotensive episodes.

Further, there is the possibility of presenting a trend in the progress of the desired parameter to the physician or staff e.g. by visual ways and means, so that the interpretation of the trend will be made by the staff first, before automatic intervention by the machine occurs. In the event of a critical trend for example, the staff are able to take other measures in good time, such as the timely injection of an isotonic saline solution.

The prognosis may alternatively be used as an input into a biofeedback system which takes countermeasures in an automated fashion, e.g. in the form of a UF reduction, an LF change, a temperature modification in the dialysis liquid or an injection of an isotonic solution.

BRIEF DESCRIPTION OF THE DRAWINGS

The invention is best understood from the following detailed description when read in connection with the accompanying drawings.

FIG. 11 shows a prognosis of the blood pressure during a therapy unit, with the formation of ensembles, and FIG. 12 shows a continuous prognosis of a complete therapy unit with an FF-NN.

DETAILED DESCRIPTION OF THE PREFERRED EMBODIMENTS

Figure 1:
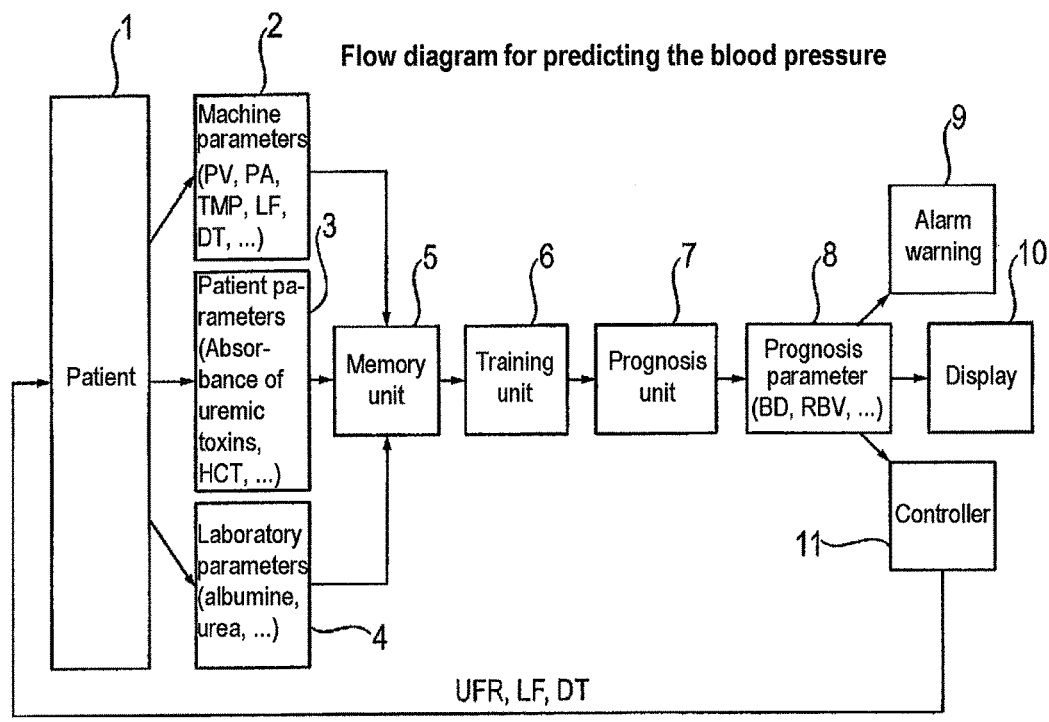
FIG. 1 shows a flow diagram for predicting blood pressure.

FIG. 1 illustrates an exemplary embodiment of the device according to aspects of the invention. The exemplary embodiment comprises a sensor or memory arrangement 2 for detecting or storing machine parameters such as the venous pressure (PV), the arterial pressure (PA), the transmembrane pressure (TMP), the conductivity (LF) of the dialysis liquid, the temperature (DT) of the dialysis liquid, and/or further parameters. These machine parameters may be directly measured by the sensor arrangement 2 on the patient 1 or on the dialysis machine, but they may already have been stored in advance. The values which are detected or delivered by the sensor arrangement or memory arrangement 2 can be stored in a memory unit 5.

Further, a sensor arrangement or memory arrangement 3 is provided, which detects patient parameters such as the absorbance of uremic toxins, of the hematocrit (HCT), etc. and may receive its input variables with corresponding measurements on the patient or on the dialysis liquid or dialysis machine.

A sensor arrangement or memory arrangement 4 is further provided for detecting or storing laboratory parameters such as of albumin, urea, etc., which may receive its input variables from the patient 1 with corresponding measurements or inputs. Just like the sensor arrangement 2, the sensor arrangements 3 and 4 also save their output signals in the memory unit 5.

On the basis of the values (such as the machine parameter, patient parameter, and laboratory parameter) which are buffered in the memory unit 5, a training unit 6 arranged downstream of the memory unit 5 is trained. The training unit 6 performs a learning phase first, whereupon it forwards the correspondingly trained, i.e. correspondingly adapted, values of the training algorithm to a prognosis unit 7.

With the integrated prognosis algorithm, the prognosis unit 7 carries out a prediction for the prognosis of the future progress of parameters which are to be determined or monitored. This calculation of the future, expected progress of the parameters which are to be predicted, in the following also referred to as prognosis parameters, takes place in the prognosis unit 7 which determines and defines the level of e.g. the blood pressure and/or the relative blood volume or any other parameters, with respect to their expected future progress. In block 8 or in further blocks 9 to 11, which are connected to block 8, the prognosis parameters can be evaluated, for instance compared to threshold values, and/or can be displayed.

In the exemplary embodiment shown in FIG. 1, block 9 is implemented as an alarm unit which delivers a warning e.g. in acoustic and/or visual form. This allows e.g. the physician or staff to carry out a quick intervention, such as a reduction in the UF rate or the supply of liquid to the patient, before an emergency situation such as a hypotensive episode even occurs.

Further, block 10 may be designed for instance as a display device showing the current progress of the prognosis parameters including the estimated progress which is to be expected in the future.

Block 11 may be designed as a controller which makes corresponding control interventions on the basis of the prognosis parameters as well as of the current parameters, such as the blood pressure or the relative blood volume, and hence controls the treatment of patient 1 in a corresponding manner.

The components 6, 7, 8 may be designed as an artificial neural network.

Patient data are detected in one, more or all exemplary embodiments. To this end, the consecutive blood pressure progress of patients is collected over a long period of time, with at least 10 subsequent therapy units of each patient being used for training. For each and every therapy unit, 48 calculated or measured blood pressure values are obtained. This means that 48*10=480 blood pressure measurements of the same patient are available for the training process.

Artificial neural networks are used in exemplary embodiments, for the prognosis of the blood pressure. It is also possible to use other prognosis methods such as support vector machines. Various network models and types are modified and tuned, so that any overfitting and underfitting can be avoided. For the sake of the better validation of the quality of the networks, more than one criterion is considered since the sole consideration of only one criterion, such as the Root Mean Square Error (RMSE) or the Mean Square Error (MSE), could result in the incorrect validation of the network or of the prognosis. This has been established in several simulations. The RMSE is the square root of the average prognosis error, i.e. of the average deviation of the prognosis from the actual observation. MSE refers to the median quadratic deviation of an estimator from the value to be estimated.

Exemplary embodiments of the invention deal with the prognosis of intradialytic parameters such as the blood pressure. The prognosis may take place with the aid of learning algorithms such as the neural networks for instance. This prognosis allows the staff to get a view of the behavior of the patient parameters in the future, so that early measures can be taken or a timely automatic intervention be carried out by the machine.

Since intradialytic morbidities are specific to a patient, it is advantageous to know the hemodynamic characteristics of the patient, e.g. the progress of at least one or more parameters in any combination, or of all the following parameters such as BD, RBV, DT, HCT, PA, PV, TMP, and/or oxygen saturation. For that reason, one, more or all exemplary embodiments of the invention provide a system which learns these hemodynamic characteristics, here also referred to as hemodynamics, in continuous fashion. Such hemodynamics can be stored after each therapy unit.

With the aid of artificial neural networks, prognoses of the progress of the hemodynamics can be made during the ongoing therapy unit, from the stored data which describe the hemodynamics of the patient in typical as well as in special situations. Artificial neural networks offer possibilities to interpret the dynamic progress of the system and to predict its future behavior. If the hemodynamic and physiological parameters of the patient are stored, their future progress can be predicted by the neural network(s).

If the artificial neural networks learn the hemodynamic characteristics of the patient, a prognosis of this characteristic is possible, depending on several parameters. If this prognosis is successful, these parameters can be controlled in good time. These parameters may be e.g. the BD and/or the RBV. As an alternative or in addition, an alarm or a warning can be triggered. A manual or automatic medicinal intervention may represent one way of stabilizing the blood pressure.

In one, more or all exemplary embodiments, prognosis of the blood pressure is the aim. The expected progress of the blood pressure can be predicted in dialysis treatment, with the aid of stored parameters. If there is a risk of hypotension, the system is able to react in good time and to adapt the UF rate before the occurrence of hypotensive situations. Normally, a reduction in the UF rate results in the stabilization of the blood pressure and hence of the hemodynamic parameters. As an alternative or in addition to the stabilization of the blood pressure, the stabilization of the prognosis of an alteration in the LF or DT may occur.

Exemplary embodiments of the invention allow the prediction of e.g. intradialytic progress of patient parameters (e.g. BD). A further reduction in blood pressure measurements can be achieved. It is possible to do without some or all of the blood pressure measurements. The early identification/prognosis of intradialytic morbidities (e.g. hypotensive episodes) is possible. Further, the early identification/prognosis of a blood pressure trend is possible. Moreover, early interaction in the event of abnormal predicted progress profiles is possible.

All the dialysis parameters which are relevant for blood pressure and used for predicting another dialysis parameter, e.g. the blood pressure, are stored after each dialysis therapy. From a certain number of stored therapy units upward, a predefined, stored neural network accesses the preselected parameters. The parameters are trained, and weights are calculated by the neural network. In the event of a new treatment, the neural network is able to calculate the expected blood pressure progress directly after connecting the patient and adjusting his/her parameters. The blood pressure progress is given in intervals of 5 minutes.

In one, more or all exemplary embodiments, various ways of controlling may be provided, e.g. retrospective, with the blood pressure measurements being carried out in predefined time intervals after the start of dialysis. During the time in which no blood pressures are measured, the blood pressures which have been calculated by the network are taken as the current blood pressures. The blood pressures calculated from the neural network can be adapted, based on their trend, to the current blood pressure trend. The process of controlling the UF rate orients itself toward the blood pressure progress and the current blood pressure, up to the current time of therapy.

Another form of control may take place in prospective fashion, a blood pressure course for the corresponding patient being calculated at the beginning of the therapy unit, i.e. after the adjustment of the patient parameters. As usual, blood pressure measurements are also carried out in predefined time intervals. The blood pressure progress is assessed up to the current point in time. In the prospective control, the future behavior of the blood pressure, which behavior is estimated from the blood pressure curve calculated specifically for said patient at the beginning of the therapy unit, is also considered and assessed in parallel. If one of the two evaluations indicates a blood pressure drop or a downward blood pressure trend, the UF rate can already be lowered, before the occurrence of said blood pressure drop or downward blood pressure trend, in order to stabilize the blood pressure.

Figure 2:
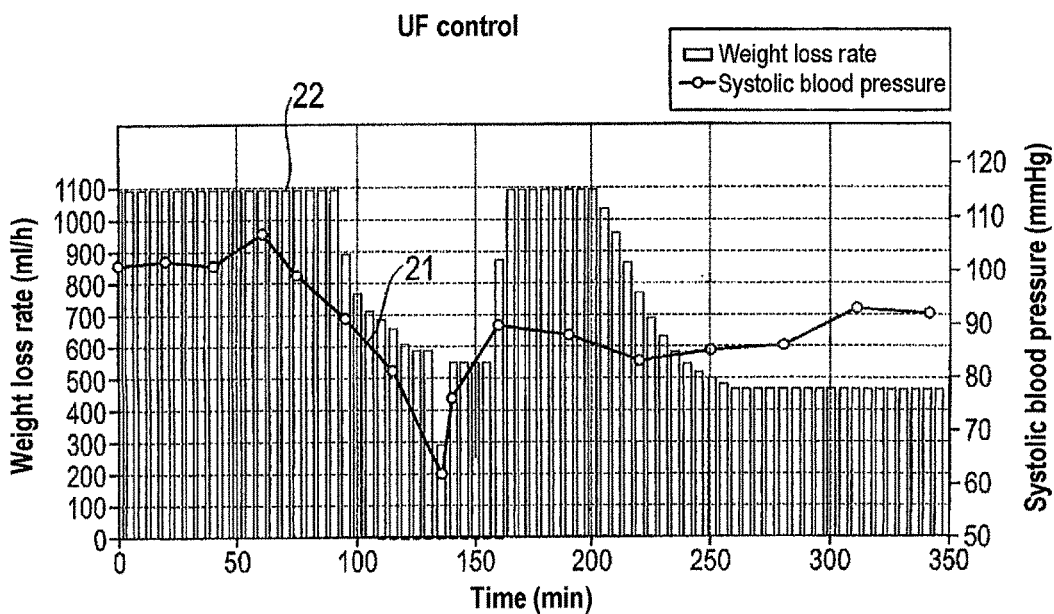
FIG. 2 shows the progress of UF control.
Figure 3:
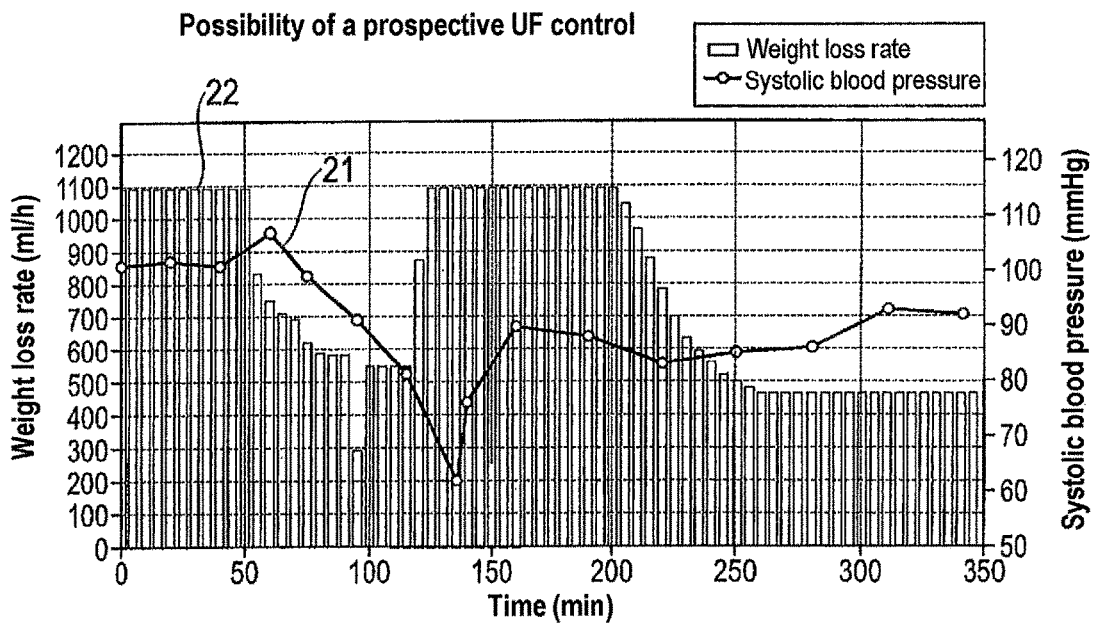
FIG. 3 shows the possibility of prospective UF control.

The time for the prospective control may be, for instance, between 5 and 60 minutes. FIGS. 2 and 3 show an illustration of the prospective control. FIG. 2 shows the retrospective control of the blood pressure, where the UF rate is not reduced until a critical limit is reached.

Curve line 21 in FIG. 2 shows the progress of the systolic blood pressure in mmHg, the round points representing the actual measured values which are determined in intervals of 20 minutes for example.

The horizontal axis shows the time in minutes, whereas the right vertical axis shows the systolic blood pressure at its current level, starting at 50 and rising to 120 mmHg. The left vertical axis shows the UF rate in ml/, the respective length of the bars indicating the corresponding UF rate (weight loss rate). The maximum limit is defined at 1100 ml/h. It can be taken from FIG. 2 that the lowering of the UF rate, in the event of falling blood pressure, occurs with some delay, i.e. takes place retrospectively.

FIG. 3 illustrates an example of the prospective UF adaptation of the UF rate as a function of the predicted blood pressure progress, in an exemplary embodiment of the invention. Analogous to the diagram according to FIG. 2, the progress of the UF rate also depends on the blood pressure progress in the illustration according to FIG. 3. However, the UF rate has already been lowered in the exemplary embodiment according to FIG. 3 before a sharp drop in the systolic blood pressure occurs. This makes it possible to achieve enhanced safety for the patient. It can also be seen in FIG. 3 that a subsequent, new rise in the blood pressure is predicted in a prospective manner and the UF rate is again increased before the blood pressure actually rises again.

In the prospective control in FIG. 3, the progress of the blood pressure is detected by the neural networks 6 to 8 and the UF rate is controlled at an early point in time in such a manner that a sharp drop in the blood pressure can be avoided.

The calculation of the prospective prognosis is carried out prior to a therapy unit, e.g. during the preparation for a dialysis therapy and with recourse to stored therapy progress. To this end, a memory medium personalized for the patient is provided, such as a patient card or a clearly definable memory area on an internal or external data carrier, or in an external memory (database), with which the dialysis machine is cross-linked. During this phase, the structure of the network can be adapted to the data, i.e. not only are the weights of a predefined network calculated, but the structure of the network is adapted too, e.g. the number of neurons or hidden layers, to ensure an optimum learning process with the existing data record. Likewise, the learning algorithm may be adapted in order to obtain optimum results. This step requires a lot of computational power since it includes the creation of many prognoses and has to be carried out at a time when the machine does not perform any functions which may be critical for the therapy unit or the patient. This is possible for example during the preparation for the dialysis therapy or even after completion of the dialysis therapy, during the sterilizing of the dialysis machine.

During the dialysis therapy, said established neural network will then also be used to evaluate new measured values which have only been recorded during the dialysis therapy, and to include them in the control in addition to the previously computed prognosis of the entire therapy.

In one, more or all exemplary embodiments, the process of learning intradialytic patient parameters is provided. An early detection of intradialytic morbidities may be of great importance for the patient since it provides, among other things, a better sense of well-being. The sense of well-being can be provided by an early reaction to the future behavior of the trained parameter (such as BD), with a manual intervention (by the staff) or an automatic intervention (by the dialysis machine) (e.g. change in the UF rate).

An artificial neural network basically consists of input neurons, hidden layers, and their activation functions and output neurons.

Figure 4:
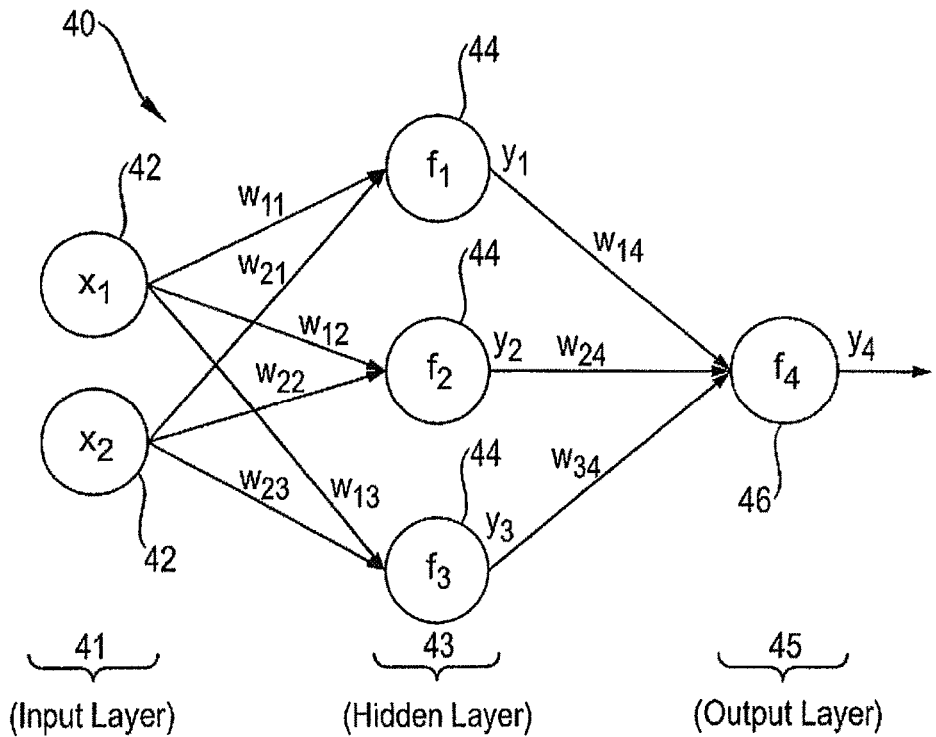
FIG. 4 is a simplified illustration of an artificial neural network.

FIG. 4 illustrates an artificial neural network 40 comprising an input layer 41 with at least two inputs 42 x1, x2, at least one hidden layer 43 comprising at least three neurons 44 $f_1$, $f_2$, $f_3$, and at least one output layer 45 with at least one output 46, $f_4$. The outputs $y_1$, $y_2$, $y_3$ of the neurons 44 and 46 and the output $y_4$ comprising the activation functions $f_1$, $f_2$, $f_3$ and $f_4$ are calculated as follows:

$$y_1 = f_1(w_{11}*x_1 + w_{21}*x_2)$$

$$y_2 = f_2(w_{12}*x_1 + w_{22}*x_2)$$

$$y_3 = f_3(w_{13}*x_1 + w_{23}*x_2)$$

$$y_4 = f_4(w_{14}*y_1 + w_{24}*y_2 + w_{34}*y_3)$$

Here, $f_1$, $f_2$, $f_3$, and $f_4$ represent the activation functions. The activation functions can be usual mathematical functions such as a Sigmoid function, threshold function, etc.

For generating the output (output signal) $y_4$, the three neuron output variables $y_1$, $y_2$, $y_3$, after being assessed (here multiplication with weights $w_{14}$, $w_{24}$, $w_{34}$), are computed, in this case added for instance.

Several network types with different numbers of hidden layers 43 and different numbers of neurons 44 have been tested. Changing the network model leads to diverging prognoses with one and the same learning algorithm. Thus, there are infinite combinations between network types, which lead to different results.

Figure 5:
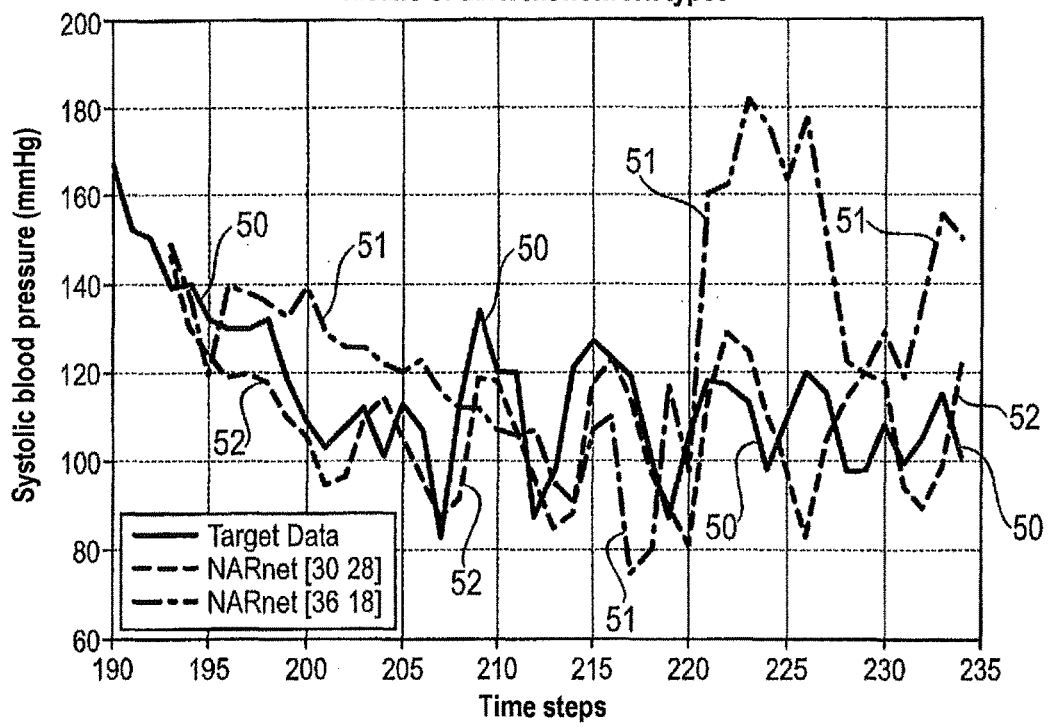
FIG. 5 shows the progress of a blood pressure prognosis with different network types.

FIG. 5 shows the result from two networks which have been trained with the same training algorithm, but have different network structures. Both networks have been trained with the Levenberg-Marquardt-Backpropagation algorithm. Curve 50 shows the actual progress of the blood pressure. Curve 52 is the result of the prognosis of a network with two hidden layers, the first layer consisting of 30 neurons and the second one of 28 neurons. Curve 51 reflects the prognosis with the aid of a network which also consists of two hidden layers, the first layer consisting of 36 neurons and the second layer of 18 neurons. Hence, FIG. 5 shows a blood pressure prognosis made by different network types.

Another factor which may result in different prognoses, is the use of different training algorithms. The process of training the networks has been carried out, inter alia, using the Bayesian Regulation-Backpropagation algorithm and the Levenberg-Marquardt-Backpropagation algorithm. The evaluation of the performance of the output, the prognosis of the blood pressure, has been evaluated with statistical ways and means, such as Root Mean Square Error (RMSE) and correlation, etc., and of visualization criteria.

Figure 7:
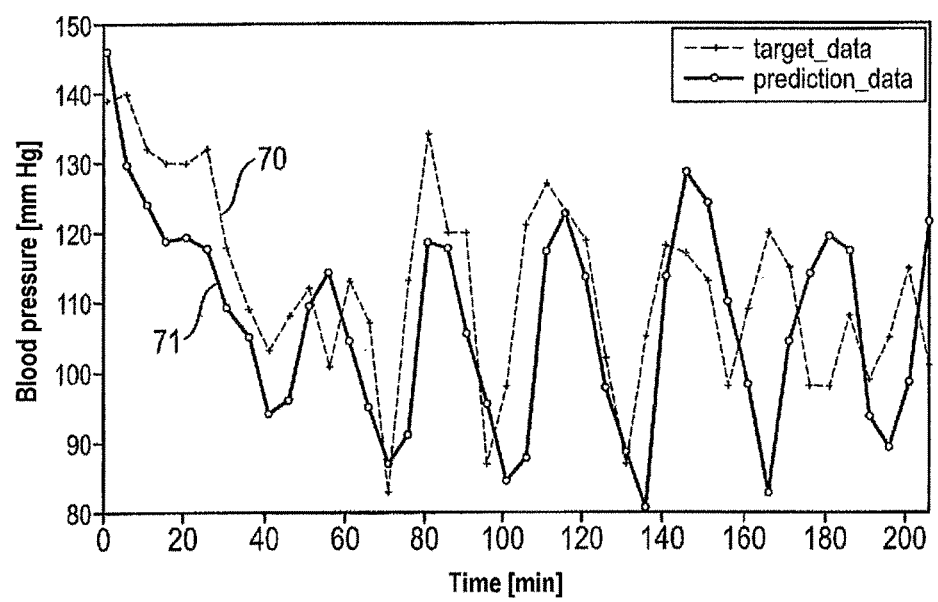
FIG. 7 shows the progress of a blood pressure prognosis with a NAR network.
Figure 8:
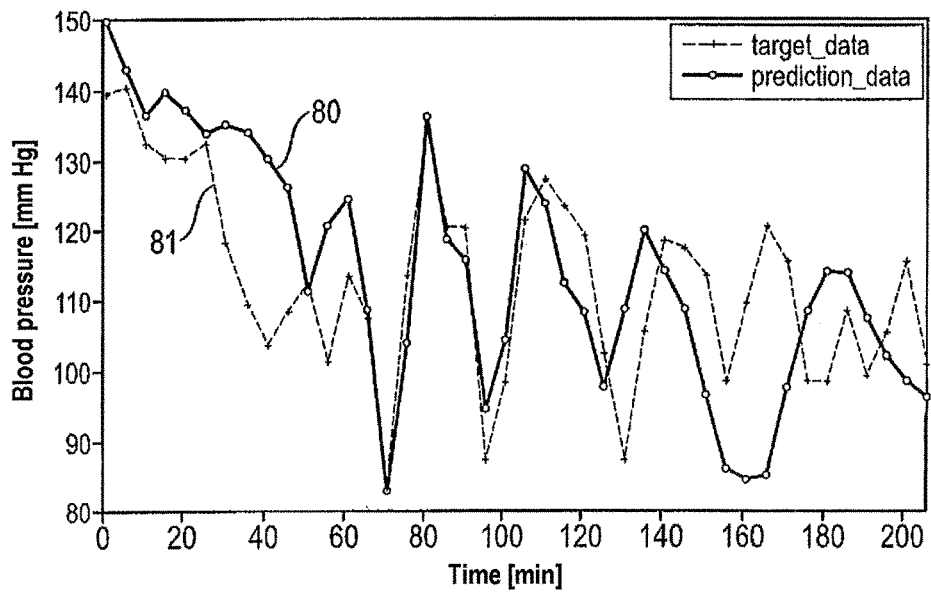
FIG. 8 shows a blood pressure prognosis with a NARX network.

FIGS. 7 and 8 illustrate diagrams of the progress of the prognosis with the nonlinear autoregressive (NAR) network and the nonlinear autoregressive exogenous (NARX) network. With NARX networks, several input and output parameters are expected.

Curves 70 and 80 show the actual progress of the blood pressure. FIG. 7 shows a BD prognosis 71 with a NAR network, whereas FIG. 8 illustrates a blood pressure prognosis 81 with a NARX network.

It can be taken from FIGS. 7 and 8 that the training with the NARX network (FIG. 8) yields better results at the beginning of the therapy unit, the NAR network (FIG. 7) exhibiting a certain shift.

Figure 6:
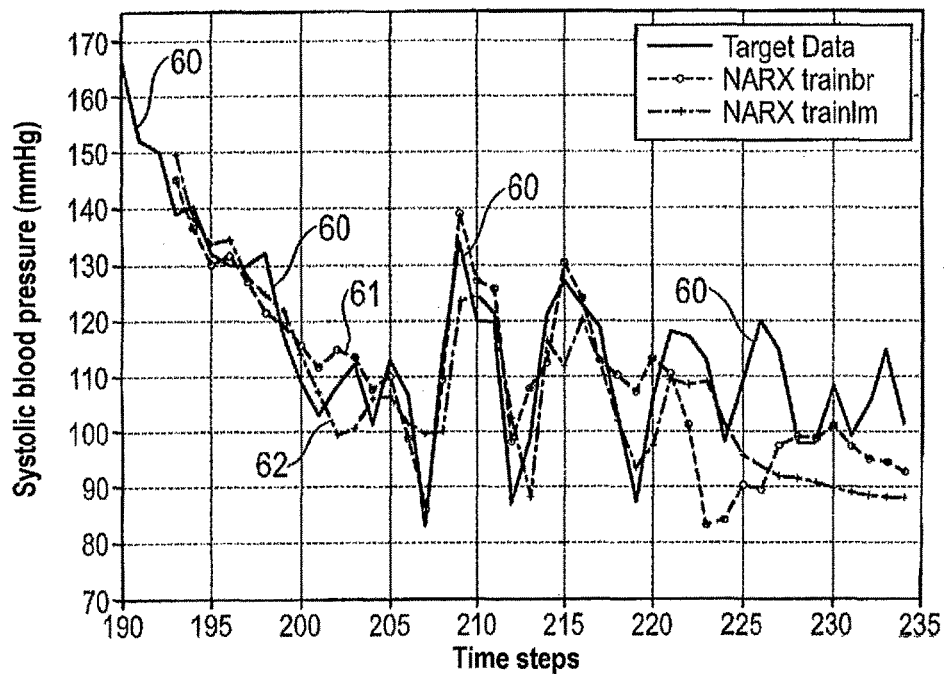
FIG. 6 shows a blood pressure prognosis with a network with different training algorithms.

FIG. 6 shows a BD prognosis made by a network using different training algorithms. Curve 60 shows the actual progress of the blood pressure. FIG. 6 depicts the prognosis of the blood pressure with both training algorithms: the Bayesian-Regulation-Backpropagation algorithm, illustrated by curve 61 with round circles, and the Levenberg-Marquardt-Backpropagation algorithm, visualized by curve 62 and provided with the "plus" symbol.

Other network types offer the possibility to take various input parameters. Such networks are referred to as nonlinear autoregressive exogenous networks (NARX). In the illustrated exemplary embodiment, two input parameters have been selected for this kind of network: the blood pressure (BD) and the UF rate. It is also possible to select a higher number of input parameters or other input parameters.

The data clearly show that the prognosis of BD values on the basis of neural networks works well for the first half of the therapy unit, but shows shortcomings in the second half. There, the deviations between the prognosis and the measured BD increase. An improvement in the quality of the prognosis is achieved in one, more or all exemplary embodiments, in that blood pressures which have been measured during the therapy unit are included in the evaluation and recalculation of the prognosis, which are carried out during the therapy unit. This takes place on the basis of the network which has been defined in advance.

In one, more or all exemplary embodiments, provision can be made to include additional input parameters and more learning techniques to further improve the prognosis.

The inclusion of the UF rate (in addition to the blood pressure) as an input parameter provided in one or more exemplary embodiments leads to an even better prognosis of the blood pressure. For this reason, several hemodynamic parameters and parameters measured by the machine are considered. These have been examined first in terms of their correlation with the blood pressure.

Figure 9:
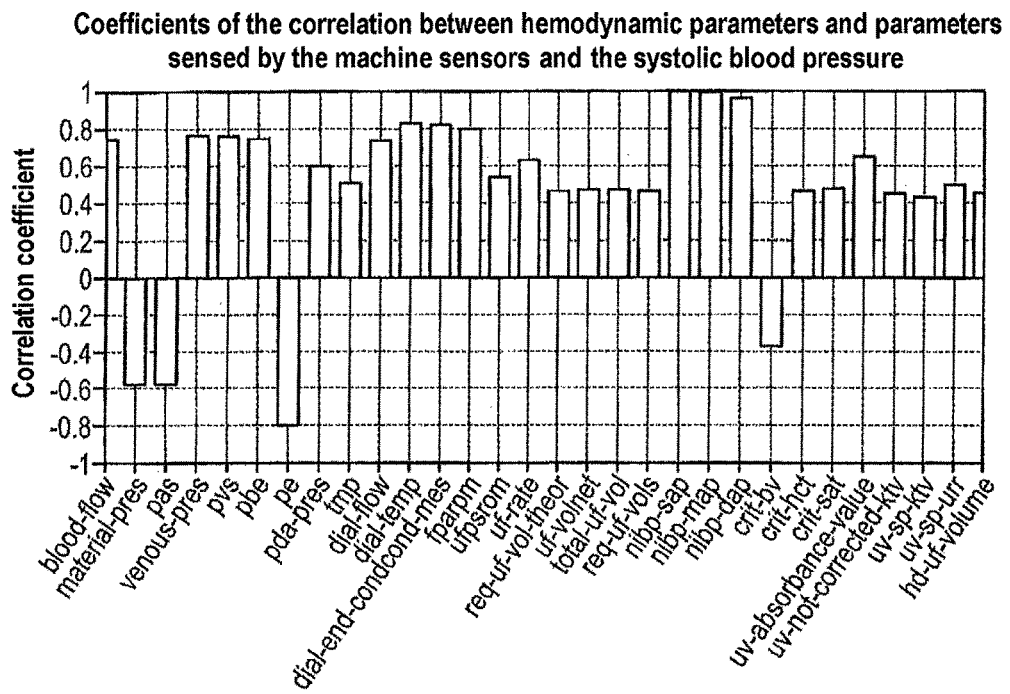
FIG. 9 shows correlation coefficients between hemodynamic parameters and parameters detected by the machine sensors with the systolic blood pressure.

FIG. 9 shows coefficients of the correlation between hemodynamic parameters and parameters recorded by the machine sensors with the systolic blood pressure. As can be seen in this diagram, 30 dialysis parameters and patient parameters have been examined for their correlation with the blood pressure. Numerous parameters had a correlation coefficient of higher than 0.5. Some of these parameters reached a correlation coefficient of approximately 0.8, these parameters not having any relationship to the blood pressure. This effect occurred due to the progress of said parameters. The progress was almost constant. From this correlation method, those parameters have been selected, which have, so to speak, a close correlation with the blood pressure.

Subsequently, various feature selection algorithms have been used on several parameters. These algorithms may include for instance the minimum-Redundancy-maximum-Relevance (mRmR) algorithm, which utilizes shared information criteria between the blood pressure and other parameters, in order to establish a certain ranking of the variables, or the Wrapper algorithm which is based on automatic learning and tries to find the best performance, by adding or deleting further variables; said best performance is then evaluated by statistical means such as the mean square error method.

Several input variables have been selected for training the network, according to expert knowledge, data analysis and feature selection algorithms, for instance one or more parameters (in any combinations) or all of the following parameters:
the ultrafiltration volume,
the arterial and venous pressure,
the hematocrit,
the relative blood volume,
the oxygen saturation,
the hemoglobin,
the ultrafiltration rate,
the heartbeat,
the absorbance of uremic toxins,
the systolic blood pressure,
the conductivity of the dialysis liquid (acid and base conductivity, pH-value),
the temperature of the dialysis liquid.

Next, generally, two algorithms of the type automatic learning and one naïve algorithm have been evaluated, the neural networks including the feed forward neural network (FF-NN) with and without tapped delayed lines (time dependency (TDL-NN)), support vector regression (SVR) with and without lag (overlapping,) and a naïve algorithm have been used, which naive algorithm extrapolates the existing blood pressure values to the next value. Cross validation has been carried out during the training. Said validation divides the courses of therapy, whose variables have to be trained, into different blocks. To give an example, the first and the last 10 therapy units are trained and the validation is applied to the therapy units therebetween, or the training is made for the first therapy units and the validation for the last ones. This achieves an increase in the training data. Thereafter, the network is selected, which has the best performance.

In the prognosis, a check has been made in terms of time dependence, i.e. as to whether there are any old variable values from the current therapy unit which have to be taken into consideration in order to predict the current blood pressure, with respect to a better performance of the prognosis by the formation of ensembles, i.e. by combining various learning algorithms and different network structures of a training algorithm, and with respect to the continuous prognosis of a therapy.

Figure 10:
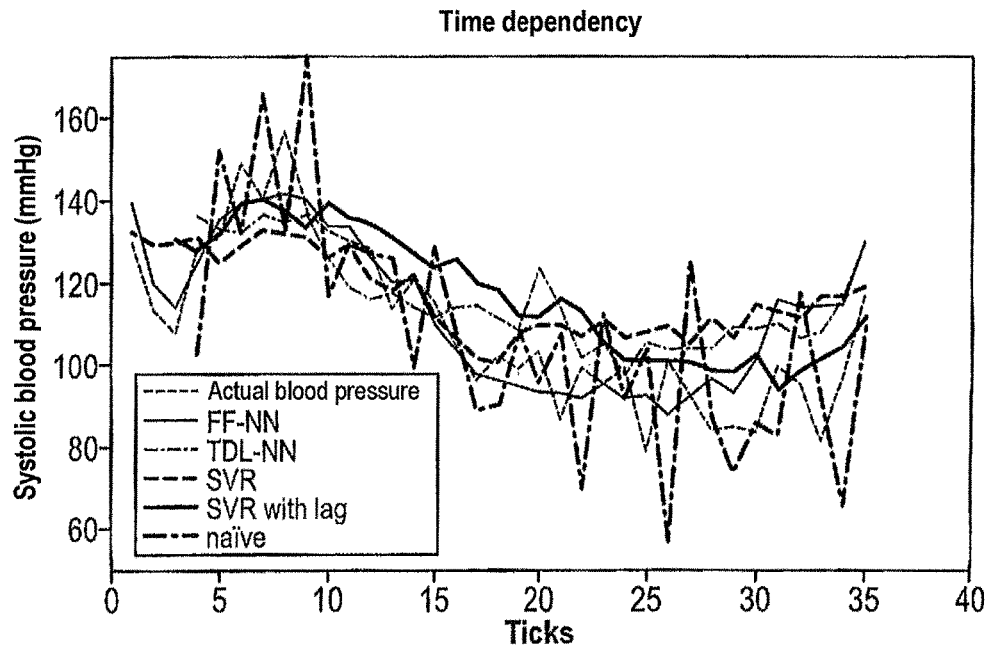
FIG. 10 shows a blood pressure prognosis with and without time lag for different learning algorithms.

Results of the individual experiments will be explained in the following:

FIG. 10 shows the time dependency and illustrates the blood pressure prognosis with and without a time delay, for different learning algorithms.

FIG. 11 shows the formation of an ensemble and gives a more detailed illustration of the prognosis of the blood pressure during a therapy unit, by the formation of ensembles.

In one, more or all exemplary embodiments, the continuous prognosis of a complete therapy may also be provided.

FIG. 12 shows the continuous prognosis of a complete therapy, with a neural network with feed forward, FF-NN (Feed Forward Neural Network).

It can be seen in FIG. 10 that the neural network involving the feed forward (Feed Forward Neural Network (FF-NN)) shows the best adaptation to the curve profile.

A good prognosis has also been achieved with the naïve algorithm. However, said prognosis fluctuates around the real blood pressure, which is due to the permanent, linear extrapolation of the last two measured blood pressures to the next 5-minute-interval.

From FIG. 10 as well as from the experiment on time dependency, it can further be concluded that blood pressure measurements can be predicted with the FF-NN without including old or current blood pressure values, as measured in the current therapy unit, in the prognosis.

Table 1 shows the results of the MSE of the experiment with time dependency for the different learning algorithms. FF-NN further shows the smallest MSE of 120.495. The naïve algorithm shows the second-best MSE. This is due to the linear extrapolation, as described above. All other MSEs show very high values and hence represent prognoses of poor quality.

TABLE 1

List of the results of the MSE from the experiment involving time dependency

| Patient | Naïve | TDL-NN | Lagged SVR | FF-NN | SVR |
|---|---|---|---|---|---|
| 1 | 62.5 | 104.4 | 188.2 | 52.4 | 243.5 |
| 2 | 162.5 | 282.8 | 350 | 153.1 | 405.2 |
| 3 | 230.6 | 245.5 | 515 | 167.5 | 132.8 |
| 4 | 108.2 | 184.9 | 425.5 | 122.1 | 267.5 |
| 5 | 148.6 | 319.8 | 325 | 119.5 | 210.1 |
| 6 | 172.5 | 167.7 | 883 | 108.2 | 172.8 |
| Mean | 147.5 | 217.5 | 447.8 | 120.5 | 238.6 |

It can be seen in FIG. 11 that almost every ensemble formation follows the progress of the blood pressure, except for the SVR lag ensemble. It can be established that the FF-NN ensemble and the SVR & FF-NN ensemble are the two curves which follow the blood pressure most accurately.

FIG. 12 illustrates the continuous prognosis of a therapy unit, in which the blood pressure is predicted every second.

In all evaluations, statistical means, such as the MSE, the hit ratio describing the spread or deviation of a predicted blood pressure with respect to the original blood pressure, and statistical algorithms such as the Aikake information criteria (AIC) and the Bayesian information criteria (BIC) are used, which assess the performance of the prognosis.

The exemplary embodiments and Figures illustrate the results which have been achieved up to now, relating to the prognosis of blood pressures and with the inclusion of blood pressure measurements and UF rates of past therapy units. However, the invention is not limited thereto.

In principle, the prognosis of other parameters of a patient, e.g. hematocrit, relative blood volume, oxygen saturation, etc., is possible with similar technology.

Nor is the number of the input parameters in the neural network limited to the parameters which are used here, and may also include (in addition to former blood pressure values and UF rates) other parameters such as hematocrit, relative blood volume, oxygen saturation, etc.

The invention claimed is:

1. A device for predicting progress in intradialytic parameters during a dialysis treatment comprising:
a memory device for storing at least one of:
patient-individual intradialytic parameters, blood pressure, laboratory parameters, or machine parameters, wherein the device is configured to set a progress of a ultrafiltration (UF)

rate as a function of a predicted progress of the blood pressure such that the UF rate is already lowered before occurrence of a drop in the blood pressure;

a prognosis unit configured to provide a prognosis of progress of the blood pressure during the dialysis treatment, wherein the prognosis unit is configured to evaluate and calculate the prognosis of the blood pressure based on the measurements of blood pressure during the dialysis treatment and the stored patient-individual intradialytic parameters, the stored laboratory parameters and/or the stored machine parameters, wherein the prognosis comprises prediction of a rise in the blood pressure in a prospective manner during the dialysis treatment; and a biofeedback system which uses the prognosis of the blood pressure progress as an input, the biofeedback system having a controller that automatically controls the UF rate in accordance with adaption of the UF rate, during the dialysis treatment based on the prognosis of progress of the blood pressure and a current blood pressure during the dialysis treatment, by increasing the UF rate before occurrence of the rise in the blood pressure.

2. The device according to claim 1, wherein further comprising a display configured to display a trend in the progress of at least one desired patient-specific parameter wherein the at least one desired patient-specific parameter includes at least one of desired blood pressure or desired relative blood volume (RBV).

3. The device according to claim 1, further comprising at least one sensor or memory arrangement for detecting or storing at least one of venous pressure (PV), arterial pressure (PA), transmembrane pressure (TMP), conductivity (LF) of the dialysis liquid, or temperature (DT) of the dialysis liquid.

4. The device according to claim 1, further comprising at least one sensor or memory arrangement for detecting or storing at least one of absorbance of uremic toxins or hematocrit (HCT).

5. The device according to claim 1 further comprising at least one sensor or memory arrangement for detecting or storing at least one of albumin or urea parameters.

6. The device according to claim 1 further comprising:
a training unit, wherein the training unit is designed to carry out a learning phase first, whereupon the training unit forwards trained values of an integrated training algorithm to the prognosis unit which makes a prediction for the prognosis of the future progress of parameters to be determined or monitored, wherein the prognosis parameters are at least one of evaluated, compared with threshold values, or displayed.

7. The device according to claim 6, wherein at least one of the training unit, the prognosis unit, or a means of forming prognosis parameters is at least one of designed as an artificial neural network or used as support vector machines.

8. The device according to claim 1, further comprising an alarm unit for outputting a warning and an estimated progress to be expected.

9. The device according to claim 1, configured to:
adapt and train, during an initial phase, the structure of a neural network comprising an input layer with at least two inputs, at least one hidden layer comprising at least three neurons, and at least one output layer with at least one output;
adapt the at least one output to the input data;
calculate the weights of a predefined network; and
alter at least one of the number of the neurons or the number of hidden layers in order to optimize learning process with an existing data record and to adapt the learning algorithm.

10. The device according to claim 9, in which the training of the networks is performed with a back propagation algorithm.

11. The device according to claim 1, wherein the parameters include at least one of the following input parameters, in addition to the blood pressure:
the ultrafiltration rate;
ultrafiltration volume;
arterial and venous pressure;
hematocrit;
relative blood volume;
oxygen saturation;
hemoglobin;
ultrafiltration rate;
heartbeat;
absorbance of uremic toxins;
systolic blood pressure;
conductivity of the dialysis liquid (acid and base conductivity, pH value); and/or
temperature of the dialysis liquid; and/or
further learning techniques.

12. A method of predicting progress in intradialytic parameters during a dialysis treatment, wherein at least one learning algorithm or at least one neural network is provided comprising:
storing, with a memory device, at least one of:
patient-individual intradialytic parameters, such as a blood pressure,
laboratory parameters, or
machine parameters wherein the one learning algorithm or the at least one neural network is configured to set a progress of a ultrafiltration (UF) rate as a function of a progress of the blood pressure such that the UF rate is already lowered before occurrence of a drop in blood pressure;
calculating and providing, with a prognosis unit, a prognosis of progress of the blood pressure, wherein the prognosis comprises the prediction of rise in the blood pressure based on the measurements of blood pressure during the dialysis treatment and the stored patient-individual intradialytic parameters, the stored laboratory parameters and/or the stored machine parameters, wherein the prognosis comprises predication of a rise in the blood pressure in a prospective manner during the dialysis treatment;
inputting, into a biofeedback system having a controller, the prognosis of progress of the blood pressure; and
automatically controlling the UF rate in accordance with adaption of the UF rate during the dialysis treatment, with the controller of the biofeedback system, based on the input prognosis of progress of the blood pressure and a current blood pressure during the dialysis treatment, wherein the controlling comprising increasing the UF rate before occurrence of the rise in the blood pressure.

13. The method according to claim 12, further comprising:
displaying a trend during the progress of the at least one desired patient-specific parameter, wherein the at least one desired patient-specific parameter includes at least one of desired blood pressure or desired relative blood volume (RBV).

14. The device according to claim 9, in which the prognosis of progress is evaluated with at least one of a nonlinear autoregressive (NAR) network or a nonlinear autoregressive exogenous (NARX) network.

15. The device according to claim 9, wherein the backpropagation algorithm is at least one of a Bayesian Regulation Backpropagation algorithm or a Levenberg-Marquardt Backpropagation algorithm.

* * * * *